United States Patent [19]
Yomtov

[11] Patent Number: 5,411,031
[45] Date of Patent: May 2, 1995

[54] IMPLANTABLE CARDIAC PATIENT MONITOR

[75] Inventor: Barry M. Yomtov, Issaquah, Wash.

[73] Assignee: InControl, Inc., Redmond, Wash.

[21] Appl. No.: 157,605

[22] Filed: Nov. 24, 1993

[51] Int. Cl.$^6$ ............................................. A61B 5/04
[52] U.S. Cl. .................................... 128/706; 128/708
[58] Field of Search ............... 128/706, 708, 696, 705, 128/702, 698

[56] References Cited

U.S. PATENT DOCUMENTS

| | | | |
|---|---|---|---|
| 3,699,949 | 10/1972 | O'Hanlon, Jr. et al. | 128/706 |
| 4,259,966 | 4/1981 | Cannon et al. | 128/706 |
| 4,777,960 | 10/1988 | Berger et al. | 128/706 |
| 4,862,361 | 8/1989 | Gordon et al. | 364/413 |
| 5,088,488 | 2/1992 | Markowitz et al. | 128/706 |

OTHER PUBLICATIONS

"Feasibility of an Implantable Arrhythmia Monitor", Leitch, et al., PACE, vol. 15, Dec., 1992, pp. 2232-2235.

"Correlations Among Time and Frequency Domain Measures of Heart Period Variability Two Weeks After Acute Myocardial Infarction", Bigger, Jr., et al., The American Journal Of Cardiology, vol. 69, Apr. 1, 1992, pp. 891-898.

"Frequency Domain Measures of Heart Period Variability and Mortality After Myocardial Infarction", Bigger, Jr., et al., Circulation, vol. 85, No. 1, Jan., 92, pp. 164-171.

"Low Heart Rate Variability and Sudden Cardiac Death", Singer, et al., Journal Of Electrocardiology, Supp. Iss., 1988, pp. S46-S53.

"Decreased Heart Rate Variability and its Association with Increased Mortality After Acute Myocardial Infarction", Kleiger, et al., The American Journal Of Cardiology, vol. 59, Feb. 1, 1987, pp. 256-262.

"An Efficient Algorithm for Spectral Analysis of Heart Rate Variability", Berger, et al., IEEE Transactions On Biomedical Engineering, vol. BME-33, No. 9, Sep., 86, pp. 900-904.

"Power Spectrum Analysis of Heart Rate Fluctuation: A Quantitative Probe of Beat-to-Beat Cardiovascular Control", Akselrod, et al., Science, vol. 213, Jul. 10, 1981, pp. 220-222.

*Primary Examiner*—William E. Kamm
*Assistant Examiner*—Scott M. Getzow
*Attorney, Agent, or Firm*—Richard O. Gray, Jr.

[57] ABSTRACT

A cardiac monitor which is fully implantable beneath the skin of a patient monitors heart rate variability of a human heart. The heart rate monitor includes at least one electrode which establishes electrical contact with the heart. During a heart monitoring period, time intervals between adjacent heart beats are determined for generating heart rate data. The heart rate data is stored in a memory which is accessed after the completion of the heart monitoring period for generating a heart rate variability factor. The heart rate variability factor is stored in memory for later transmission to a nonimplanted external receiver.

26 Claims, 4 Drawing Sheets

IMPLANTABLE CARDIAC PATIENT MONITOR

BACKGROUND OF THE INVENTION

The present invention is directed to an implantable cardiac patient monitor. The present invention is more particularly directed to an implantable cardiac patient monitor which, in addition to monitoring for various arrhythmias and ischemia of the heart, is also capable of monitoring heart rate variability of the heart.

Changes in beat-to-beat variability of the heart as an indicator of cardiac autonomic status, has been shown in the literature to be a predictor of long-term survival after acute myocardial infarction. Changes in beat-to-beat variability of the heart has also been shown to be a predictor of heart transplantation rejection.

More specifically, it has been shown in the literature that lower heart rate variability in patients who have had a recent myocardial infarction may be more vulnerable to sudden cardiac death (SCD). However, many patients who have progressive coronary artery disease may also have asymptomatic (silent) myocardial infarctions. If undetected, the risk of a sudden cardiac death episode in these patients may increase. The only way to discern a change in this risk factor is through a cardiac monitor capable of continuously monitoring heart rate variability which would provide this necessary feedback. Unfortunately, the prior art has not provided such a continuously monitoring system.

Patients who have undergone a heart transplant are presently monitored for transplant rejection by endocardial biopsy at regular prescribed time intervals. Endocardial biopsies are both costly and can only provide clinical feedback at the prescribed intervals. The hearts of patients with transplanted hearts have low heart rate variability due to the lack of neural connections. The literature has shown that an increase in heart rate variability within these patients also provides an indication of transplant rejection. Hence, there is a need in the art for a cardiac monitor capable of providing continuous monitoring of the heart rate variability of these patients. Such a cardiac monitor could reduce the number and frequency of such expensive, invasive procedures. In addition, with such a cardiac monitor, a rejection episode may be detected earlier than heretofore possible thus providing more immediate treatment to the patient suffering from heart transplantation rejection.

SUMMARY OF THE INVENTION

The invention provides a cardiac monitor for monitoring heart rate variability of a human heart. The monitor is fully implantable beneath the skin of a patient and includes electrode means for establishing electrical contact with the heart, timing means for timing a heart monitoring period, and sensing means coupled to the electrode means for generating an electrocardiogram of each heart beat of the heart occurring during the heart monitoring period. The monitor further includes time interval determining means for determining time intervals between adjacent heart beats, heart rate data generating means responsive to the time intervals for generating heart rate data, memory means for storing the heart rate data, and factor generating means responsive to the stored heart rate data for generating a heart rate variability factor. The memory means stores the heart rate variability factor and telemetry means transmits the heart rate variability factor stored in the memory means to a nonimplanted external receiver.

The present invention further provides a cardiac monitor for monitoring heart rate variability of a human heart wherein the monitor is fully implantable beneath the skin of a patient. The monitor includes timing means for timing successive heart monitoring periods, electrode means for establishing electrical contact with the heart, R wave detecting means coupled to the electrode means for detecting R waves of the heart during each heart monitoring period, and interval determining means responsive to the R wave detecting means for determining the time intervals between adjacent R waves. The monitor further includes data generating means responsive to the time intervals for generating heart rate data, memory means for storing the heart rate data, and factor generating means responsive to the completion of each heart monitoring period and the stored heart rate data for generating a heart rate variability factor for each heart monitoring period. The memory means stores the heart rate variability factors and telemetry means transmits the heart rate variability factors stored in the memory means to a nonimplanted external receiver.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
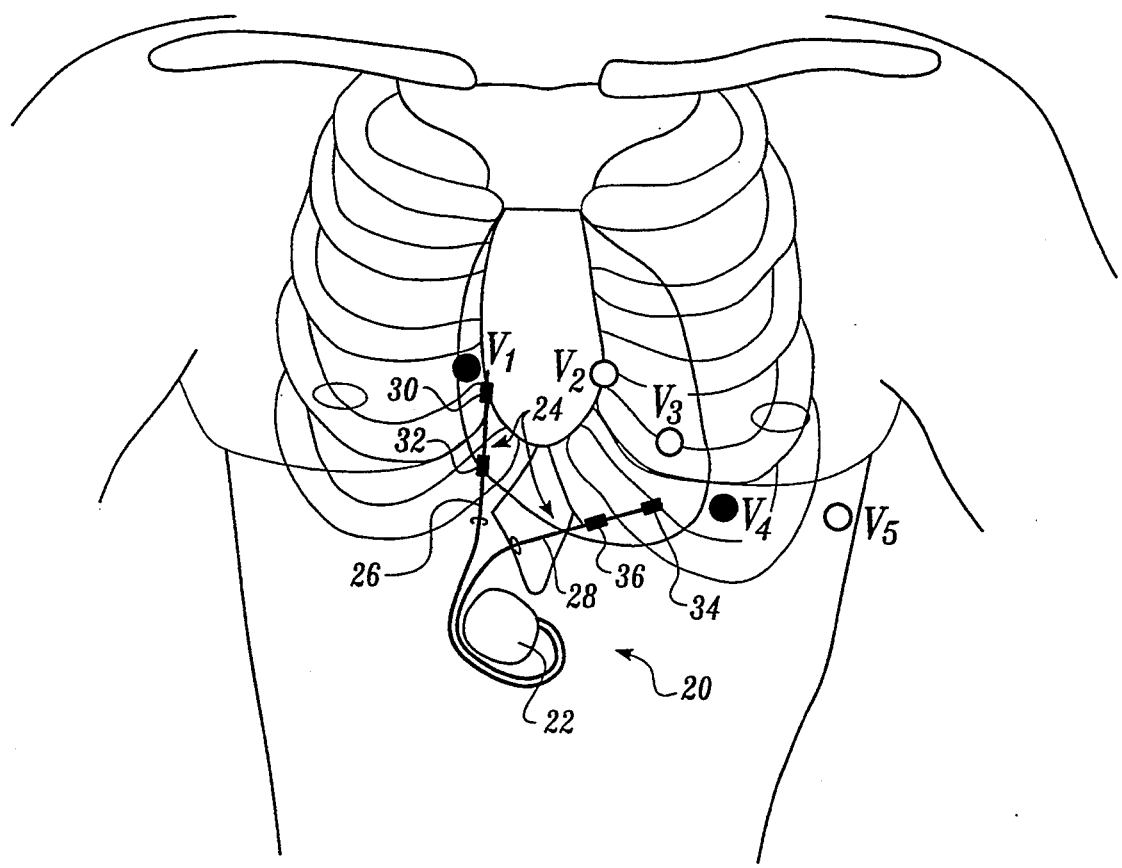
FIG. 1 is a schematic front plan view of the human abdomen and chest illustrating a preferred implantation site of an implantable cardiac monitor embodying the present invention.

Referring now to FIG. 1, it is a schematic front plan view of the human abdomen and chest illustrating a preferred implantation site of an implantable cardiac monitor 20 embodying the present invention. The implantable cardiac monitor 20 generally includes an enclosure 22 and electrode means 24. The enclosure 22, as will be described hereinafter, includes electronic circuitry for monitoring heart activity and generating data indicative of the heart rate variability of the heart.

The enclosure 22 is preferably implanted beneath the skin in the right sub-costal region below the rib cage. The electrode means 24 preferably includes leads 26 and 28 which are subcutaneously implanted beneath the skin. The leads 26 and 28 include electrodes 30, 32 and 34, 36 respectively for establishing electrical contact with the heart in non-touching relation thereto. Illustrated in FIG. 1 are six standard locations for external exploring electrodes used for routine clinical electrocardiography designated $V_1$ through $V_6$. The electrodes 30, 32, 34, and 36, as illustrated, are implanted in the precordial area in close proximity to the $V_1$ through $V_4$ locations. Each of the leads 26 and 28 is a catheter lead with the electrodes 30, 32, 34, and 36 being conductive ring-shaped electrodes.

Figure 2:
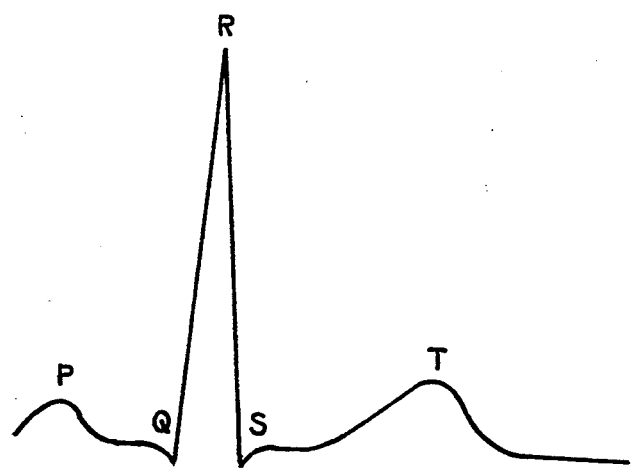
FIG. 2 is a graphic representation of a typical or normal ECG waveform showing the conventional nomenclature for the various portions thereof.

Referring now to FIG. 2, it provides a graphic representation of a typical or normal electrocardiogram (ECG) waveform showing the conventional nomenclature for the various portions thereof. The beginning of a heart beat is initiated by a P wave which is normally a small positive wave. Following the P wave there is an ECG waveform portion which is substantially constant in amplitude. This substantially constant portion will have a time duration on the order of, for example, 120 milliseconds.

The QRS complex of the ECG then normally occurs after the substantially constant portion with a Q wave which is normally a small negative deflection which is then immediately succeeded by the R wave which is a rapid positive deflection. The R wave generally has an amplitude greater than any other waves of the ECG signal and will have a spiked shape of relatively short duration with a sharp rise, a peak amplitude, and a sharp decline. The R wave may have a duration on the order of 40 milliseconds. However, as described in U.S. Pat. No. 5,313,953, which issued on May 24, 1994 in the names of Barry M. Yomtov and Paul E. Kreyenhagen for IMPLANTABLE CARDIAC PATIENT MONITOR, which patent is assigned to the assignee of the present invention and incorporated herein by reference, the cardiac monitor 20 discriminates between normal heart beats of the type illustrated in FIG. 1, for example, and abnormal heart beats which are referred to herein as ventricular beats which are ectopic beats originating in a ventricle of the heart and which are generally characterized by an R wave having a duration which is greater than the duration of the normal R wave morphology of the patient being monitored.

Following the R wave, the QRS complex is completed with an S wave. The S wave may be generally characterized by a small inflection in the ECG signal.

Following the S wave is the T wave which is separated from the S wave by the ST segment. The amplitude of the ST segment, in a healthy heart, is generally approximately equal to the baseline following the P wave and preceding the Q wave. The T wave is relatively long in duration of, for example, on the order of 150 milliseconds. Following the T wave, which concludes the heart beat, is a substantially constant amplitude until the next P wave occurs.

As will be seen hereinafter, each electrode of the cardiac monitor 20 is coupled to a respective input amplifier. Each input amplifier generates an ECG signal for each heart beat from which the R wave is detected. The ECG signals are also digitized by an analog to digital converter and stored in a memory through a direct memory access. Following each heart beat, a microprocessor of the cardiac monitor processes adjacent R waves to determine the time interval between adjacent heart beats and to generate data indicative of the heart rate of the heart being monitored. The microprocessor performs its processing for each heart beat after the digital samples of the ECG signals are stored and during the time following the T wave of its heart beat and before the P wave of the next heart beat. In processing the stored data, the microprocessor distinguishes between normal heart beats (normal sinus heart beats) and abnormal heart beats (ventricular beats) so that, for time domain heart rate variability analysis, only heart rate data associated with adjacent normal heart beats is generated. The heart rate data generated during a heart monitoring period is stored in memory. At the end of the heart monitoring period, the microprocessor generates a heart rate variability factor based upon the stored heart rate data.

For time domain heart rate variability analysis known as pNN50, to be described hereinafter, the monitoring period may be as long as twenty-four hours. For another form of time domain heart rate variability analysis known as SDANN Index, consecutive sub-monitoring periods, as short as five minutes, may be employed for generating an average interval for each sub-monitoring period and at the end of twenty-four hours, the standard deviation of those averages may be generated as the heart rate variability factor for the monitoring period. For a still further form of time domain heart rate variability analysis known as SDNN Index, the standard deviation of the normal heart beat intervals occurring during each monitoring sub-period is determined. After twenty-four hours, the mean of the standard deviation is generated as the heart rate variability factor. Hence, for time domain heart rate variability analysis, heart rate data is continuously generated and stored. However, only the data required to generate a final desired heart rate variability factor is stored to conserve memory space. Once a heart rate variability factor is generated, it is stored in memory for later transmission to an external receiver by telemetry.

As will also be seen hereinafter, the implantable cardiac monitor also makes provision for external frequency domain heart rate variability analysis. If such analysis is desired, during limited times in which the heart rate data is also being generated for frequency domain analysis, the determined heart beat intervals for normal beats are stored in memory. For a ventricular beat, the intervals for the heart beats surrounding the ventricular beat are interpolated and also stored. Thereafter, when the stored intervals are to be processed externally for frequency domain analysis, all of the stored intervals may be transmitted to an external receiver by telemetry.

Figure 3:
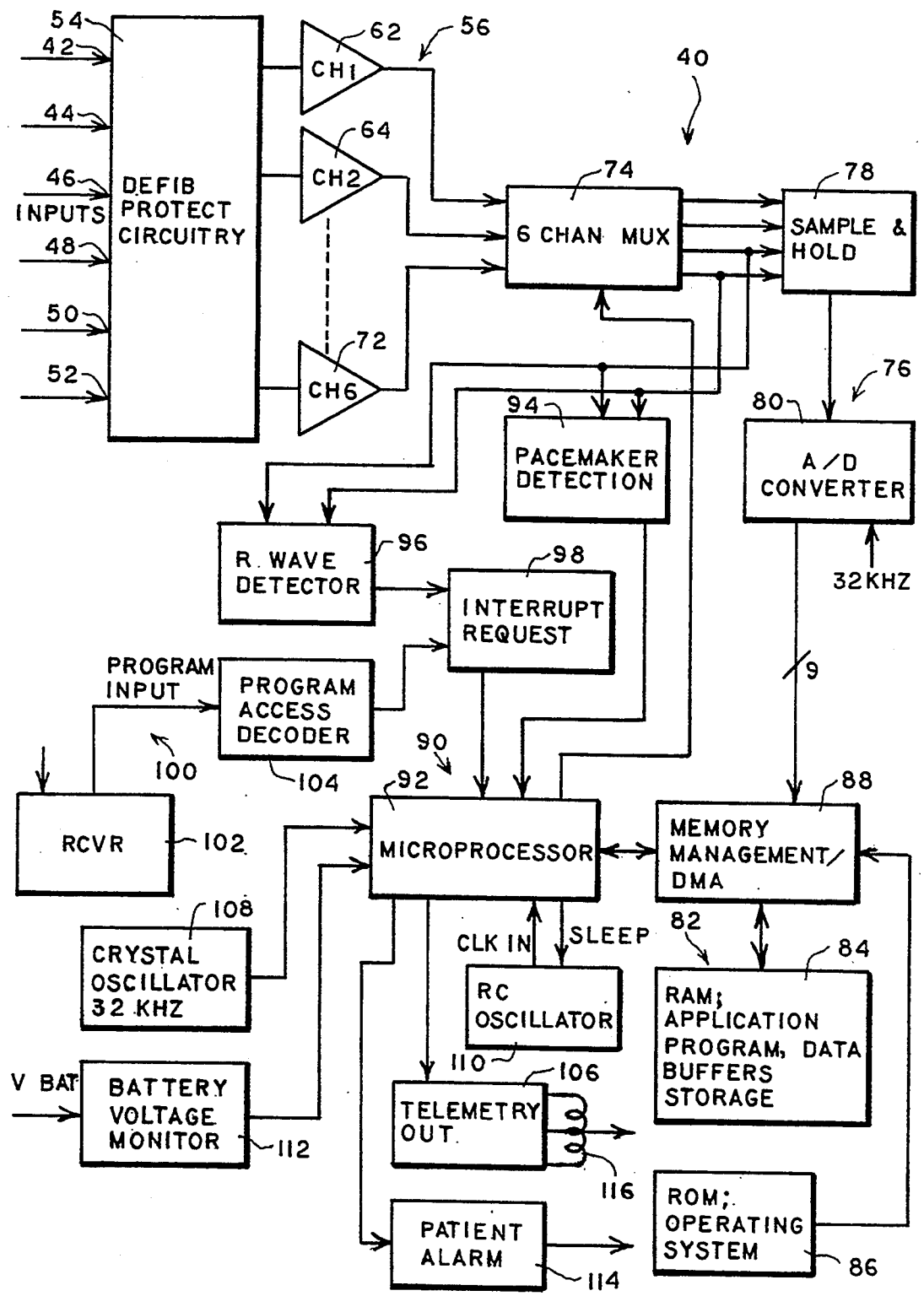
FIG. 3 is a detailed schematic block diagram of the internal circuitry of an implantable cardiac monitor embodying the present invention.

Referring now to FIG. 3, it illustrates in schematic block diagram form, the internal circuitry of the implantable cardiac monitor 20 of FIG. 1 which is contained within the enclosure 22. The cardiac monitor circuitry 40 generally includes a plurality of inputs 42, 44, 46, 48, 50, and 52 which are arranged to be coupled to the electrodes 30, 32, 34, and 36 of the electrode means 24 illustrated in FIG. 1. As will be noted, six such inputs are provided for accommodating up to six electrodes. As will be seen hereinafter, in accordance with this preferred embodiment, up to four of the heart activity signals received at inputs 42, 44, 46, 48, 50, and 52 may be utilized for heart rate variability monitoring of the heart. The particular inputs to be utilized in monitoring the physiology of the heart may be externally programmable to allow the cardiologist flexibility in selecting those inputs which provide the best heart activity signals.

The circuitry 40 further includes defibrillation protection circuitry 54, a sensing means 56 comprising a plurality of input amplifiers with each input amplifier corresponding to a respective given one of the inputs. To that end, input amplifier 62 corresponds to input 42, input amplifier 64 corresponds to input 44, and input amplifier 72 corresponds to input 52. The input amplifiers corresponding to inputs 46, 48, and 50 are not illustrated so as to not unduly complicate the figure.

The circuitry 40 further generally includes a multiplexer 74, a data generating means 76 including a sample and hold 78 and an analog to digital converter 80, a memory means 82 including a random access memory 84 and a read only memory 86, and a direct memory access 88. The circuitry 40 further includes a processing means 90 including a microprocessor 92, a pacemaker detector 94, an R wave detector 96, and an interrupt request 98. The circuitry 40 still further generally includes a telemetry input means 100 including a receiver 102 and a program access decoder 104, a telemetry output 106, a crystal oscillator 108, and an RC oscillator 110. Lastly, the circuitry generally includes a battery monitor 112 and a patient alarm 114.

The defibrillation protection circuitry 54 protects the circuitry 40 from defibrillating energy which may be applied to the heart by a ventricular defibrillator. Such circuitry may include zener diodes in a manner well known in the art.

The inputs 42, 44, 46, 48, 50, and 52 are coupled to the inputs of the input amplifiers 62, 64, and 72 through the defibrillation protection circuitry 54. Each of the input amplifiers generates an electrocardiogram representing the heart beats of the heart detected by its corresponding electrode. The outputs of the input amplifiers 62, 64, and 72 are coupled to the multiplexer 74 which, responsive to external programing, selects up to four outputs of the input amplifiers to be utilized for monitoring the heart. As a result, the output of the multiplexer 74 includes four channels which are coupled to the sample and hold 78. As illustrated in the Figure, the electrocardiograms provided by the first and second channels of the multiplexer are used for detecting R waves and are thus coupled to the R wave detector 96. In addition, the first and second channels of the multiplexer 74 are also coupled to the pacemaker detector 94 for detecting stimuli applied to the heart by a pacemaker. Such pacemaker detection is provided so that only those electrocardiograms corresponding to spontaneous or natural heart beats of the heart are utilized by the processing means 90 for processing the electrocardiogram data. To that end, the pacemaker detector 94 is coupled to the microprocessor 92 to cause the microprocessor to disregard electrocardiograms which correspond to heart activity resulting from a pacemaker stimulus.

The first and second channels of multiplexer 74 along with the third and fourth channels of multiplexer 74 are coupled to the sample and hold 78. The sample and hold 78 is coupled to the analog to digital converter 80 which converts the analog electrocardiogram signals being held by the sample and hold 78 to digital samples one at a time in succession. To that end, the analog to digital converter 80 is coupled to the crystal oscillator 108 which provides clocking signals at a rate of, for example, 32 kilohertz. The crystal oscillator 108 continuously provides the clocking signals so that the sample and hold 78 and analog to digital converter 80 continuously generate digitized electrocardiogram data. The digital samples provided by the analog to digital converter 80 are preferably multiple-bit digital samples containing, for example, nine bits. The digital samples of the electrocardiograms are provided to the direct memory access 80 which continuously stores the electrocardiogram digital samples in the random access memory 84.

In addition to storing the digital samples of the electrocardiograms of each of the four utilized channels, the random access memory 84 also stores operating instructions for microprocessor 92 which define the executions to be performed by the microprocessor 92 for processing the electrocardiogram digital samples for in turn generating various characterizing data of the physiology of the heart. The microprocessor 92, as described in copending application Ser. No. 07/820,580 incorporated herein by reference, responsive to the operating instructions provided by random access memory 84 and the electrocardiogram digital samples may be arranged for monitoring arrhythmias of the heart, ischemia, or both arrhythmias and ischemia in addition to the heart rate variability monitoring contemplated by the present invention depending upon the manner in which the cardiac monitor is externally programmed. The random access memory 84 also includes storage locations which are utilized for buffering data to temporarily store data such as heart rate data and storage locations for storing data such as heart rate variability factors generated by the microprocessor 92 which are to be more permanently stored and made available to the cardiologist upon external interrogation for the transmission of such data by the telemetry output 106 to an external receiver.

The read only memory 86, in a manner well known in the microprocessor art, stores basic operating system instructions for the microprocessor 92. Such basic system operating instructions may include instructions which permit the microprocessor 92 to perform the input programming and the output telemetry functions for transmitting data to and from an external receiver, to permit the microprocessor to perform reset executions, and to permit the microprocessor to perform self-check operations, for example.

As previously mentioned, the microprocessor 92 processes the detected R waves and the stored electrocardiogram digital samples and generates characterizing data indicative of the physiology, such as heart rate variability, of the heart. Because the cardiac monitor circuitry 40 is implantable, it is preferably powered by a depletable power source such as a battery. To conserve on battery power, the microprocessor 92 only processes data at selected times, as for example, between heart beats. When the microprocessor 92 processes data, the RC oscillator 110 provides the microprocessor 92 with clock pulses to control the execution rate of the microprocessor 92. When the microprocessor is not processing data, the RC oscillator 110 is selectively turned off.

To "wake-up" the microprocessor 92, to permit the microprocessor 92 to process data, the R wave detector 96 detects an R wave from the first channel, the second channel, or both the first and second channels. After a predetermined time duration following the detection of an R wave, the R wave detector 96 provides a trigger signal to the interrupt request 98. The interrupt request 98 services the trigger signal to cause the microprocessor 92 to start the RC oscillator 110 and commence processing data. The predetermined time period or delay in providing the trigger by the R wave detector 96 may be, for example, a period of 300 milliseconds, for example, following the R wave detection to cause the microprocessor 92 to commence processing data prior to the next heart beat. As a result, in accordance with this preferred embodiment, the random access memory 84 need only store the electrocardiogram data for a single electrocardiogram for each of the four channels. After the processing of the electrocardiogram data, the new electrocardiogram digital samples for the next heart beat may be utilized to write over the electrocardiogram data stored during the previous heart beat. However, as is further disclosed in application Ser. No. 07/820,580, digital samples of selected electrocardiograms may be more permanently stored for later retrieval by the cardiologist. The digital samples of the electrocardiograms to be more permanently stored may be moved by the microprocessor 92 to a more permanent storage location within the random access memory 84 prior to the occurrence of the next heart beat. The more permanently stored electrocardiograms may be the electrocardiograms occurring at the onset and termination of various arrhythmic episodes such as ventricular tachycardia or ischemic episodes.

The patient alarm 114 is provided to alert the patient to a low battery condition, a serious arrhythmic event, or a serious ischemic event and to notify the patient that the patient should call the cardiologist. The patient alarm 114 may take the form of a piezo electric buzzer for example or a low energy stimulus which may be felt by the patient but not of sufficient energy to stimulate the heart. Such alarms may also be coded to permit the patient to inform the cardiologist as to the type of event which prompted the alarm.

For programming the modalities of the cardiac monitor, including the heart rate variability monitoring modality, the receiver 102 receives a signal generated externally. The programming signal may be coded in a known manner to define the modality of the cardiac monitor. The programming signals received by receiver 102 are decoded by the program access decoder 104 and conveyed to the interrupt request 98. The interrupt request 98 services the decoded programming signals and provides the same to the microprocessor 92. The microprocessor 92 then stores the programming operating conditions in the random access memory 84 and is also conditioned for fetching only those program instructions from the random access memory 84 for executing the selected programmed modalities. For example, the random access memory 84 may store a first set of operating instructions to cause the microprocessor to detect arrhythmias, a second set of operating instructions to cause the microprocessor to detect ischemia, and a third set of operating instructions to cause the microprocessor 92 to detect heart rate variability.

To transmit characterizing data, such as the heart rate variability factors and heart beat intervals as contemplated by the present invention, generated by the microprocessor 92 to an external receiver, the telemetry output 106 may include a radio frequency transmitter of the type well known in the art which transmits a radio frequency carrier which is pulse code modulated. The radio frequency signal generated by the telemetry output 106 is radiated from an antenna such as antenna coil 116. A preferred location of the telemetry antenna coil 116 for efficiently conveying the characterizing data to an external receiver is fully described in application U.S. Pat. No. 5,313,953.

Lastly, the battery monitor 112 monitors the voltage of the battery which powers the cardiac monitor. When the battery voltage decreases to a threshold limit, the battery monitor 112 will provide a signal to the microprocessor 92 indicating that battery power will soon be depleted. In response to such a signal, the microprocessor 92 may cause the patient alarm 114 to provide a suitable alarm to the patient to prompt the patient to notify the cardiologist of the low battery condition. In addition, the microprocessor 92 may store the battery condition in the random access memory 84 and time stamp the low battery condition so the cardiologist upon retrieving the characterizing data from the random access memory will be informed as to the time in which the battery monitor 112 first detected the low battery condition.

Figure 4:
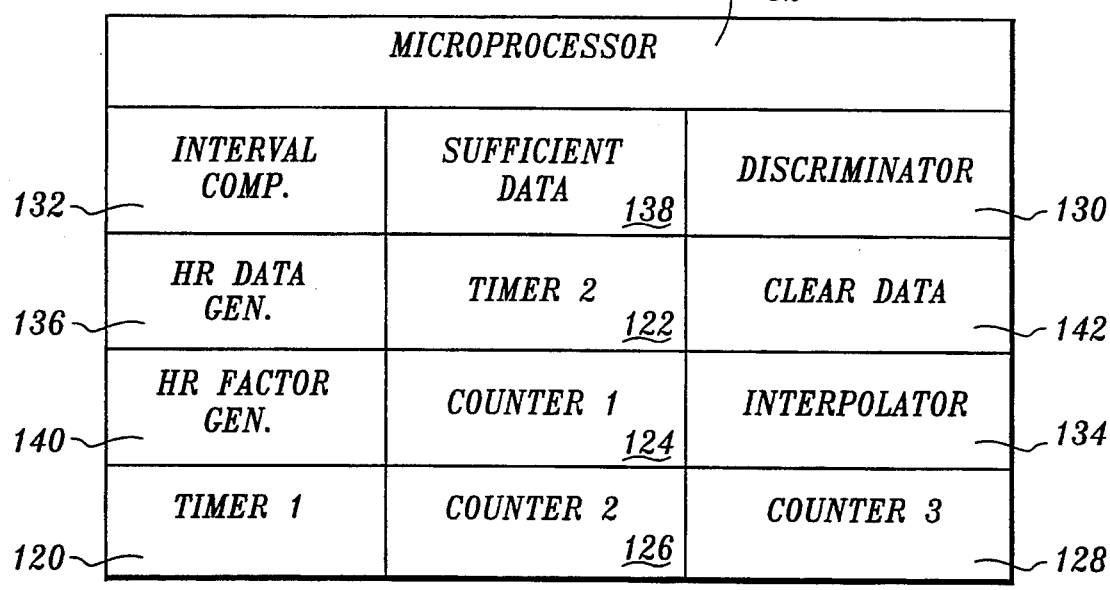
FIG. 4 is a more detailed block diagram of the microprocessor of FIG. 3 illustrating the various functional stages of the microprocessor when operating pursuant to stored operating instructions for providing heart rate variability monitoring in accordance with a preferred embodiment of the present invention.

Referring now to FIG. 4, it illustrates the microprocessor 92 in greater detail. When the heart rate variability monitoring modality is enabled through external programming, the microprocessor 92 is caused to fetch and execute the third set of instructions. In doing so, the microprocessor 92 is configured to include a plurality of functional stages to that end. Those function stages are illustrated in FIG. 4.

A first functional stage is first timer 120. The first timer 120 times the duration of each heart rate monitoring period. For example, if pNN50 time domain heart rate variability analysis is to be performed, the first timer will time successive twenty-four hour monitoring periods.

A second timer 122 times heart rate monitoring subperiods. For example, if SDANN Index or SDNN Index time domain heart rate variability analysis is to be performed, timer 122 will time successive five-minute monitoring subperiods. Concurrently with timer 122 timing the five-minute monitor sub-periods, timer 120 will time a twenty-four hour monitoring period.

Another functional stage is a first counter 124. The first counter is incremented with each detected R wave. Hence, at the end of a monitoring period, the counter 124 will contain the number of all heart beats occurring during the monitoring period.

A second counter 126 is incremented each time a normal sinus heart beat is immediately preceded by another normal sinus heart beat. Hence, counter 126, at the end of each monitoring period, contains the total number of adjacent normal sinus heart beats.

A third counter 128 may be employed in performing pNN50 time domain heart rate variability analysis. To that end, the counter 128 is incremented whenever a currently analyzed heart beat interval between adjacent normal sinus heart beats deviates from an immediately preceding heart beat interval between adjacent normal sinus heart beats by an amount greater than a predetermined time, such as 50 ms, for example. Hence, at the end of a monitoring period, the counter 128 will contain the number of heart beat intervals between adjacent normal sinus heart beats which deviated from the heart beat interval of their immediately preceding heart beat intervals by an amount greater than the predetermined time.

Another functional stage of microprocessor 92 is the discriminator stage 130. As previously mentioned, only adjacent normal sinus heart beats are analyzed for generating heart beat intervals and heart rate data for time domain heart rate variability analysis while, for frequency domain heart rate variability analysis data collection, the heart beat intervals associated with ventricular beats are interpolated and stored along with heart beat intervals associated with adjacent normal sinus heart beats. Hence, the discriminator stage 130 is implemented to discriminate between normal sinus heart beats and ventricular beats.

The foregoing discriminating process is described in detail in U.S. Pat. No. 5,313,953. In general, as described therein, the abnormal heart beat is an ectopic ventricular heart beat wherein the heart beat originates in the ventricles rather than at the sinus node where a normal heart beat originates. Such a ventricular heart beat is characterized by an R wave having a longer duration than the R wave of a normal sinus heart beat. In order to facilitate the discrimination between a normal sinus heart beat and a ventricular beat, the discriminator stage 130 of the microprocessor 92 establishes a template corresponding to the electrocardiogram of a normal sinus heart beat of the patient. The discriminator stage 130 of the microprocessor 92 generates such a template upon the initialization of the cardiac monitor and revises the template at spaced apart time intervals to account for changes in the normal morphology of the patient's heart over time. Such revisions to the template may be made at periodic intervals of, for example, 15 seconds, or alternatively may be made after a predetermined number of heart beats have occurred, such as, for example, 15 heart beats. In generating the template, the microprocessor averages a first predetermined number of data samples for each data point for a corresponding number of electrocardiograms and ascribes to each data point a maximum limit and a minimum limit.

To determine if a heart beat is a normal sinus heart beat or an abnormal heart beat, the electrocardiogram generated by amplifiers 62 and 64 are used. The stored data samples of the electrocardiograms are aligned with the template. Then, the deviation between the data samples of the electrocardiograms and the template for each data point are summed in a running total until each data sample of the electrocardiograms has been compared to the template. Thereafter, the running sum is normalized to derive a number indicative of the difference between each of the electrocardiograms and the template. If that number is greater than a predetermined threshold for either electrocardiogram, the heart beat corresponding to those electrocardiograms is classified as an abnormal heart beat. Conversely, if that number is less than the predetermined threshold for both electrocardiograms, the heart beat corresponding to those electrocardiograms is classified as a normal sinus heart beat.

To revise the template, the microprocessor averages the data samples for only those electrocardiograms corresponding to classified normal sinus heart beats and then computes a weighted average which is then averaged with the previous template. As a result, revisions to the template will accurately represent the gradual changes in heart morphology of a patient over time.

An interval computation stage 132 determines the time intervals between adjacent normal heart beats. When an R wave is detected by the R wave detector 96 from the electrocardiogram signals provided by either amplifier 62 or amplifier 64, the interrupt request 98, after the delay imposed by the R wave detector of, for example 300 milliseconds, applies a trigger signal to the microprocessor 92. The interval computation stage 132 then keeps time until another trigger signal is received. If the discriminator determines that the two adjacent trigger signals resulted from normal sinus heart beats, the interval computed by the computation stage 132 is temporarily stored in memory. If the two adjacent trigger signals did not result from normal sinus heart beats, the discriminator 130 then causes the stored determined time interval to be used by the interpolating stage 134 for interpolating the heart beat intervals before and after the ventricular beat.

The interpolating stage 134 interpolates heart beat intervals associated with ventricular beats during those times when interval data for external frequency domain analysis is being generated. In doing so, the interpolating stage 134, responsive to the discriminator, averages the heart beat intervals occurring immediately before and immediately after the ventricular beat. The two averaged heart beat intervals are then stored in memory as the heart beat intervals associated with the ventricular beat. The interpolated intervals and the non-interpolated intervals are stored together until the heart rate data collection for external frequency domain analysis is completed. Thereafter, this data, upon external command, is transmitted to a nonimplanted receiver for use by the cardiologist for external frequency domain heart rate variability analysis.

A heart rate data generator 136 generates heart rate data for interval time domain heart rate variability analysis. For example, for pNN50 heart rate variability analysis, the heart rate data generator 136 compares the time interval determined by stage 132 for each heart beat with the time interval determined by stage 132 for the immediately preceding heart beat. If the current heart beat interval deviates from the immediately preceding heart beat interval by an amount greater than a predetermined time, for example 50 milliseconds, the heart rate data generator 136 generates an incrementing signal to increment the third counter 128.

To conserve memory space, when heart beat interval data is not being collected for external frequency domain heart rate variability analysis, only the last and current heart beat intervals are retained in memory for use by the heart rate data generator for pNN50 time domain heart rate variability analysis. However, for other forms of time domain heart rate variability analysis, such as SDANN Index or SDNN Index heart rate variability analysis, the heart beat intervals generated by stage 132 during each sub-monitoring period, of for example five minutes, are retained in memory. After each sub-monitoring period, the heart rate data generator 136 generates, for SDANN Index heart rate variability analysis, the average of the intervals stored during the sub-monitoring period, and for SDNN Index, the standard deviation of the intervals stored during the sub-monitoring period. The averages or standard deviations are then stored for later use and the time intervals stored are overwritten with new intervals during the next sub-monitoring period.

A sufficient data stage 138 determines if sufficient normal heart beat intervals have occurred to permit either sub-monitoring period heart rate data (standard deviation or average) to be computed after each sub-monitoring period or a final heart rate variability factor to be computed after a heart rate variability monitoring period is completed. For example, one criterion that may be imposed is the requirement that at least fifty percent of the heart beat intervals be resulting from adjacent normal sinus heart beats during the respective period. For example, for pNN50 heart rate variability analysis, stage 138 will determine if at least fifty percent of the heart beats during the last twenty-four hours were adjacent normal sinus heart beats. For SDANN Index or SDNN Index, stage 138 may make the same determination based upon the heart beats occurring during the last sub-monitoring period of five minutes, for example.

The stage 138 utilizes the counts maintained in the first counter 124 and the second counter 126. As previously mentioned, the first counter 124 maintains the count of all heart beats occurring during the last sub-monitoring or monitoring period and the second counter 126 maintains the count of the number of adjacent normal sinus heart beats. Hence, the stage 138 divides the number of counts in the second counter 126 by the number of counts in the first counter 124. If the result is equal to or greater than a preselected factor, for example 0.5, sufficient adjacent normal sinus heart beats have occurred during the sub-monitoring or monitoring period to permit the heart rate data generator 136 to generate the standard deviation or average or to permit the heart rate variability factor generator 140 to compute a heart rate variability factor.

The heart rate variability factor generator 140 generates a final heart rate variability factor. For pNN50 time domain heart rate variability analysis, for example, the generator 140 generates the percentage of the heart beat intervals which differed by more than a predetermined time, for example 50 milliseconds, from immediately preceding heart beat intervals during a monitoring period, for example twenty-four hours. In accordance with this preferred embodiment, the generator 140 divides the count maintained in counter 128 by the count maintained in counter 126 and multiples this result by 100 to provide the heart rate variability percentage factor.

For SDANN Index analysis, the generator 140 computes a heart rate variability factor by computing the standard deviation of the average normal heart beat intervals for all five-minute segments (five-minute sub-monitoring periods) for a twenty-four hour monitoring period. For SDNN Index analysis, the generator 140 computes a heart rate variability factor by computing the mean of the standard deviation of the normal heart beat intervals for all five-minute segments (five-minute sub-monitoring periods) for a twenty-four hour monitoring period. As previously mentioned, the average for the SDANN Index analysis and the standard deviation for the SDNN Index analysis are previously computed by the heart rate data generator 136 and stored in memory.

The heart rate variability factors generated by generator 140 are stored in memory. Thereafter, the factors may be transmitted, through telemetry, to an external receiver in response to an external command.

The last functional stage is a clear data stage 142. The clear data stage 142 clears from memory including the counters 124, 126, and 128 the stored heart rate data responsive to the generator 140 generating the time domain heart rate variability factor or in response to the stage 138 determining that an insufficient number of adjacent normal sinus heart beats have occurred during the relevant monitoring or sub-monitoring period.

Figure 5:
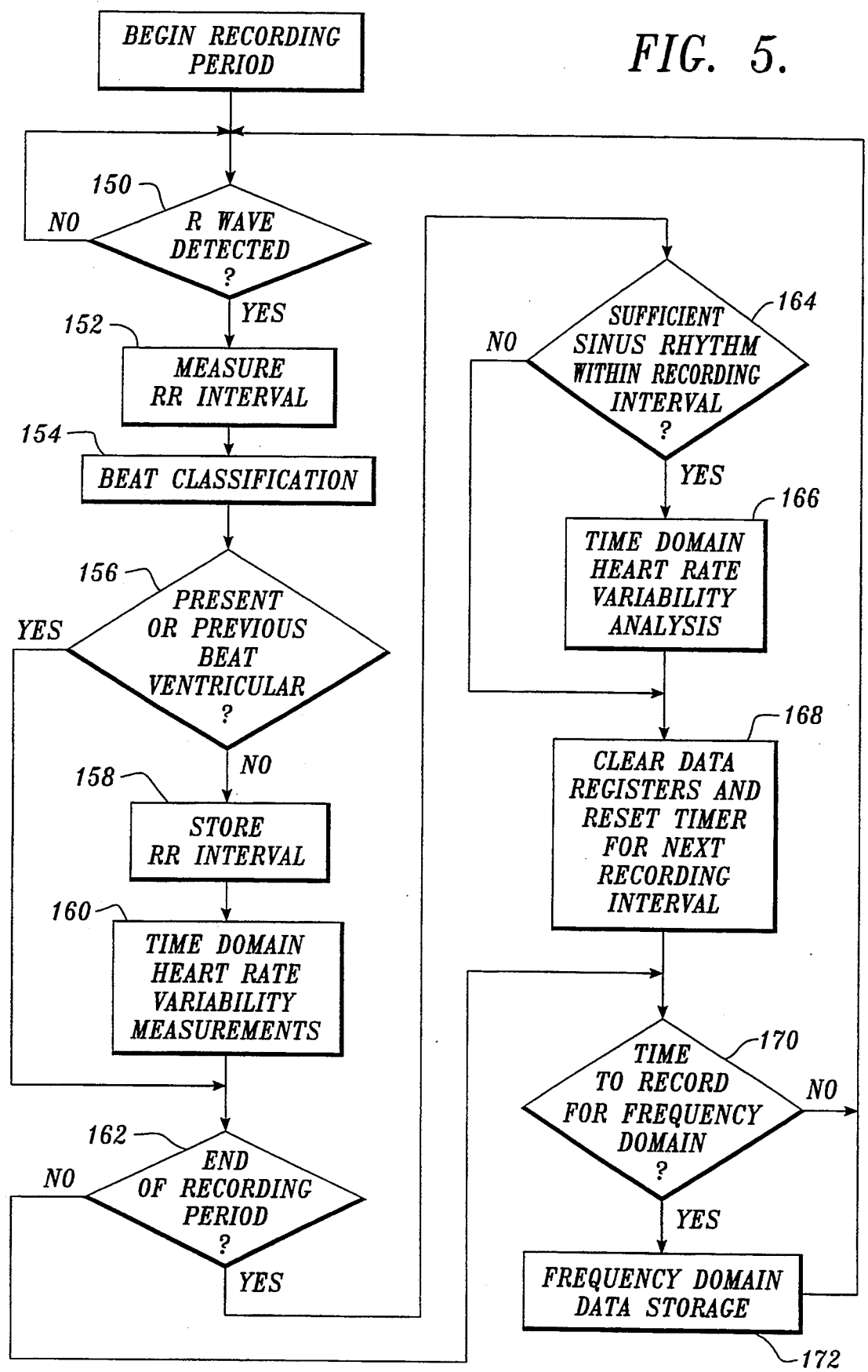
FIG. 5 is a flow diagram illustrating the manner in which the implantable cardiac monitor of FIG. 3 may be implemented for time domain heart rate variability monitoring of the human heart and for initiating data storage for frequency domain heart rate variability analysis.

Referring now to FIG. 5, it is a flow diagram illustrating the manner in which the implantable cardiac monitor of FIG. 3 may be implemented for monitoring heart rate variability of the human heart and for initiating data storage for external frequency domain heart rate variability analysis. The flow diagram of FIG. 5 is particularly adapted for the previously referred-to pNN50 time domain heart rate variability analysis.

As previously mentioned, the microprocessor 92 processes the data associated with each heart beat between heart beats. The processing begins, in accordance with this preferred embodiment, 300 milliseconds after the R wave of a heart beat is detected. This provides sufficient time for all of the significant heart beat activity to be stored in the form of an electrocardiogram in memory 84. Before the sequence begins, if a new heart monitoring period is being initiated, the first timer 120 is started. Then, the heart rate variability monitoring sequence begins with step 150 wherein the microprocessor 92 determines if an R wave has been detected by the R wave detector 96.

Once the microprocessor 92 determines that the R wave detector 96 has detected an R wave, the interval computation stage 132 determines the R to R interval for the last heart beat in step 152. Although the R wave detection as seen by the microprocessor is delayed by 300 milliseconds, each R wave detected is delayed by the same 300 millisecond time period. As a result, the interval computation stage 132 is capable of determining the R to R interval accurately. Also with the detection of an R wave by the microprocessor in step 150, the first counter 124 is incremented for counting the total number of heart beats occurring during the heart rate monitoring period.

After the R to R interval of the last heart beat is determined in step 152, the discriminator 130 then classifies the heart beat being processed as either a normal sinus heart beat or a ventricular beat in step 154. The discriminator 130 discriminates between a normal sinus heart beat and a ventricular beat in a manner as previously described herein and as more fully described in application Ser. No. 07/820,580.

After classifying the heart beat presently being processed as either a normal sinus heart beat or a ventricular beat, the microprocessor then determines in step 156 if either the present beat being processed or the immediately preceding beat was a ventricular beat. If either the heart beat currently being processed or the immediately preceding heart beat was a ventricular beat, the process skips to step 162 which will be described hereinafter. However, if neither the heart beat currently being processed or the immediately preceding heart beat was a ventricular beat, the second counter 126 is incremented and the heart beat interval determined in step 152 is stored in memory in accordance with step 158. The negative determination in step 156 signifies that adjacent normal sinus heart beats have occurred and that the interval determined in step 152 may be utilized for the time domain heart rate variability analysis.

After the heart beat interval is stored in step 158, the heart rate data generator 136 then generates heart rate variability data associated with the heart beat currently being processed. In accordance with this preferred embodiment wherein the cardiac monitor is performing time domain pNN50 heart rate variability analysis, the heart rate data generator 136 determines if the heart beat interval for the heart beat currently being processed deviates by more than 50 milliseconds from the immediately preceding heart beat interval. If it does, the heart rate data generator 136 will increment the third counter 128.

When the microprocessor completes step 160 by the heart rate data generator 136 either incrementing or not incrementing the third counter 128, the microprocessor then in step 162 interrogates the first timer 120 to determine if the end of the heart rate monitoring period has been reached. If the heart rate monitoring period is completed, the sufficient data stage 138 next determines in step 164 if a sufficient number of adjacent normal sinus heart beats have occurred during the heart monitoring period. If there has not been a sufficient number of adjacent normal sinus heart beats during the heart monitoring period, the microprocessor then jumps to step 168 whereupon the clear data stage 142 clears all of the heart rate data stored in the memory 84 and in the counters 124, 126, and 128. Also at this time, the first timer 120 is reset to prepare the cardiac monitor for initiating a new heart monitoring period.

If in step 164 it is determined that there have been a sufficient number of adjacent normal sinus heart beats during the heart monitoring period, the heart rate variability factor generator 140 of the microprocessor 92 then generates a heart rate variability factor in step 166. In generating the heart rate variability factor in step 166, and in accordance with the pNN50 analysis previously described, the heart rate variability factor generator determines the percentage of the adjacent normal heart beats having intervals which deviated by more than 50 milliseconds from their respective immediately preceding heart beat intervals. In accordance with the preferred embodiment, this is accomplished by dividing the count maintained in the third counter 128 by the count maintained in the counter 126 and multiplying that result by 100 to derive the percentage of the heart beat intervals resulting from normal sinus heart beats which differed by more than 50 milliseconds from their immediately preceding heart beat intervals resulting from normal sinus heart beats over the heart rate monitoring period which, in accordance with this preferred embodiment, is a twenty-four hour period.

When the heart rate variability factor generator 140 generates the heart rate variability factor, the heart rate variability factor is stored in memory. This makes the heart rate variability factor available to the cardiologist for transmission by the cardiac monitor telemetry 106 upon an external command initiated by the cardiologist. Since a number of heart rate monitoring periods may elapse between such external commands, the cardiologist will be able to obtain each heart rate variability factor generated at the end of each heart monitoring period. Further, in accordance with known prior art techniques, each heart rate variability factor may be time stamped so that the cardiologist will be informed as to when each heart rate variability factor was generated.

Once the heart rate variability factor is generated by the heart rate variability factor generator 140, the clear data stage 142 clears all of the heart rate variability data and counters 124, 126, and 128. In addition, the first timer 120 is reset to initiate the beginning of a new heart rate monitoring period.

Figure 6:
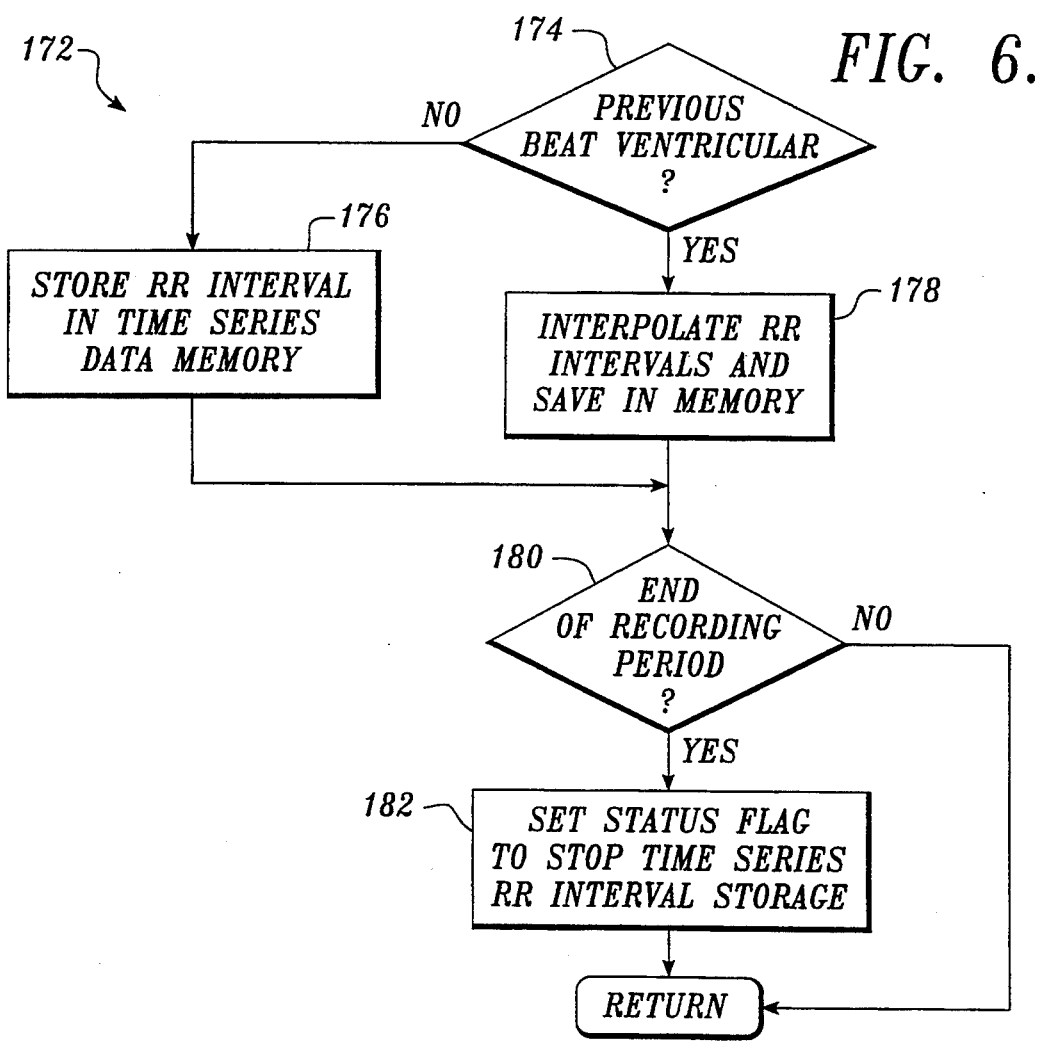
FIG. 6 is a flow diagram illustrating the manner in which the implantable cardiac monitor of FIG. 3 may be implemented for generating and storing data for frequency domain heart rate variability analysis in accordance with the present invention.

Before initiating a new monitoring period however, the microprocessor performs step 170 wherein it determines if it is time to record for external frequency domain heart rate variability analysis. The time to record such heart rate data may be maintained by the second timer 122. The microprocessor performs step 170 during each processing period either after heart rate data associated with time domain analysis has been cleared due to the heart rate variability factor generator 140 generating a heart rate variability factor in step 166 or after a determination in step 162 that the heart monitoring period has not yet completed. If in either case it is not time to record for frequency domain analysis, the microprocessor returns to step 150 to detect another R wave. However, if it is time to record heart rate data for external frequency domain heart rate variability analysis, the microprocessor proceeds to the routine identified by reference character 172 and which is shown in greater detail in FIG. 6.

In performing the frequency domain data storage routine 172, the microprocessor first determines if the previous beat was a ventricular beat in step 174. If the previous beat was not a ventricular beat, the microprocessor then in step 176 stores the R to R interval determined in step 152 (FIG. 5) in a time series within a permanent memory portion of the memory 84. If the previous beat was ventricular, the interpolating stage 134 then interpolates the R to R intervals for the heart beat being currently processed and the immediately preceding beat in step 178 and stores those intervals within the time series permanent memory portion of memory 84.

After either step 176 or step 178, the microprocessor then in step 180 interrogates the second timer 122 to determine if the data gathering period for the external frequency domain heart rate variability analysis has been completed. If it has not been completed, the microprocessor returns to step 150 (FIG. 5) to detect another R wave. If the heart rate data gathering period has been completed, the microprocessor then in step 182 sets a status flag to stop the time series R to R interval data storage. At this time, all heart beat intervals for both adjacent normal sinus heart beats which are not interpolated and the heart beat intervals associated with ventricular beats which are interpolated are contained within the memory 84 and in a condition to be transmitted to an external receiver upon an external command of the cardiologist for external frequency domain heart rate variability analysis.

As will be appreciated by those skilled in the art, the heart rate data gathering period for external frequency domain heart rate variability analysis may be significantly shorter than the heart rate monitoring period for time domain analysis. For example, the data gathering period for external frequency domain heart rate variability analysis may be between five minutes to three hours, for example. During the time in which such heart interval data is to be gathered, as will be discerned from the flow diagrams of FIG. 5 and FIG. 6, the cardiac monitor performs time domain analysis and heart interval analysis for frequency domain analysis for each heart beat.

While a particular embodiment of the present invention has been shown and described, modifications may be made, and it is therefore intended in the appended claims to cover all such changes and modifications which fall within the true spirit and scope of the invention.

What is claimed is:

1. A cardiac monitor for monitoring heart rate variability of a human heart, said monitor being fully implantable beneath the skin of a patient and comprising:

electrode means for establishing electrical contact with the heart;
   timing means for timing a heart monitoring period;

sensing means coupled to said electrode means for generating an electrocardiogram of each heartbeat of the heart occurring during said heart monitoring period;

time interval determining means responsive to said electrocardiograms for determining time intervals between adjacent heartbeats;

heart rate data generating means responsive to said time intervals for generating heart rate digital data;

memory means for storing said heart rate digital data;

factor generating means responsive to said timing means and said stored heart rate digital data for generating a digital heart rate variability factor at the end of said heart monitoring period;

said memory means for storing said digital heart rate variability factor; and telemetry means for transmitting said digital heart rate variability factor stored in said memory means to a nonimplanted external receiver.

2. A cardiac monitor as defined in claim 1 wherein said electrode means includes at least one electrode adapted to be implanted subcutaneously beneath the skin of a patient in non-touching relation to the heart.

3. A cardiac monitor as defined in claim 1 further including an R wave detector and wherein said time interval determining means is responsive to said R wave detector for determining time intervals between successive R waves.

4. A cardiac monitor as defined in claim 1 wherein said timing means times successive heart monitoring periods, and wherein said factor generating means generates a heart rate variability factor at the end of each said heart monitoring period.

5. A cardiac monitor as defined in claim 4 wherein each said heart monitoring period is between five minutes and twenty-four hours.

6. A cardiac monitor for monitoring heart rate variability of a human heart, said monitor being fully implantable beneath the skin of a patient and comprising:
electrode means for establishing electrical contact with the heart;
timing means for timing a heart monitoring period;
sensing means coupled to said electrode means for generating an electrocardiogram of each heartbeat of the heart occurring during said heart monitoring period;
time interval determining means responsive to said electrocardiograms for determining time intervals between adjacent heartbeats;
second timing means for timing monitoring sub-periods during said heart monitoring periods;
heart rate data generating means responsive to said time intervals for generating first heart rate data and responsive to said first heart rate data for generating second heart rate data at the end of each said monitoring sub-period;
memory means for storing said first and second heart rate data;
factor generating means responsive to said stored second heart rate data for generating a digital heart rate variability factor:
said memory means for storing said heart rate variability factor; and
telemetry means for transmitting said heart rate variability factor stored in said memory means to a nonimplanted external receiver.

7. A cardiac monitor for monitoring heart rate variability of a human heart, said monitor being fully implantable beneath the skin of a patient and comprising:
electrode means for establishing electrical contact with the heart;
timing means for timing a heart monitoring period;
sensing means coupled to said electrode means for generating an electrocardiogram of each heartbeat of the heart occurring during said heart monitoring period;
time interval determining means responsive to said electrocardiograms for determining time intervals between adjacent heartbeats;
heart rate data generating means responsive to said time intervals for generating heart rate data;
memory means for storing said heart
discriminating means for discriminating between normal sinus heart beats and ventricular heart beats;
factor generating means responsive to said stored heart rate data for generating a heart rate variability factor;
said memory means for storing said heart rate variability factor; and
telemetry means for transmitting said heart rate variability factor stored in said memory means to a nonimplanted external receiver.

8. A cardiac monitor as defined in claim 7 wherein said factor generating means includes time domain analysis means for generating a time domain heart rate variability factor and is responsive to only heart rate data associated with adjacent normal sinus heart beats for generating said time domain heart rate variability factor.

9. A cardiac monitor as defined in claim 8 further including sufficient data determining means for determining if a sufficient number of adjacent normal sinus heart beats have occurred during said heart monitoring period and wherein said factor generating means generate said time domain heart rate variability factor only if said sufficient number of adjacent normal sinus heart beats have occurred.

10. A cardiac monitor as defined in claim 9 further including clearing means for clearing said stored heart rate data from said memory means after generating said time domain heart rate variability factor or after said sufficient data determining means determines that said sufficient number of adjacent normal sinus heart beats have not occurred.

11. A cardiac monitor as defined in claim 9 wherein said sufficient number of adjacent normal sinus heart beats is equal to or greater than fifty percent of said heart beats being adjacent normal sinus heart beats.

12. A cardiac monitor as defined in claim 7 further including interpolating means responsive to said discriminating means for interpolating heart beat time intervals associated with ventricular heart beats.

13. A cardiac monitor as defined in claim 12 further including second memory means for storing all said time intervals and wherein said telemetry means transmits all said time intervals stored in said second memory means to an external receiver to permit frequency domain processing of all said time intervals.

14. A cardiac monitor as defined in claim 13 wherein said telemetry means is responsive to a command originating from external to the skin of a patient for transmitting all said time intervals stored in said memory means.

15. A cardiac monitor for monitoring heart rate variability of a human heart, said monitor being fully implantable beneath the skin of a patient and comprising:
   timing means for timing successive heart monitoring periods;
   electrode means for establishing electrical contact with the heart;
   R wave detecting means coupled to said electrode means for detecting R waves of the heart, during each said heart monitoring period;
   interval determining means responsive to said R wave detecting means for determining the time intervals between adjacent R waves;
   data generating means responsive to said time intervals for generating heart rate digital data;
   memory means for storing said heart rate digital data;
   factor generating means responsive to the completion of each said heart monitoring period timed by said timing means and said stored heart rate digital data for generating a digital heart rate variability factor for each said heart monitoring period;
   said memory means for storing said digital heart rate variability factors; and
   telemetry means for transmitting said digital heart rate variability factors stored in said memory means to a nonimplanted external receiver.

16. A cardiac monitor as defined in claim 15 wherein said electrode means includes at least one electrode adapted to be implanted subcutaneously beneath the skin of a patient in non-touching relation to the heart.

17. A cardiac monitor as defined in claim 15 wherein said heart monitoring periods have a duration between five minutes and twenty-four hours.

18. A cardiac monitor for monitoring heart rate variability of a human heart, said monitor being fully implantable beneath the skin of a patient and comprising:
   timing means for timing successive heart monitoring periods;
   electrode means for establishing electrical contact with the heart;
   R wave detecting means coupled to said electrode means for detecting R waves of the heart, during each said heart monitoring period;
   interval determining means responsive to said R wave detecting means for determining the time intervals between adjacent R waves;
   second timing means for timing monitoring sub-periods during said heart monitoring periods;
   generating means responsive to said time intervals for generating first heart rate data and responsive to said first heart rate data for generating second heart rate data at the end of each said monitoring sub-period;
   memory means for storing said first and second heart rate data;
   factor generating means responsive to the completion of each said heart monitoring period and said second stored heart rate data for Generating a heart rate variability factor for each said heart monitoring period;
   said memory means for storing said heart rate variability factors: and
   telemetry means for transmitting said heart rate variability factors stored in said memory means to a nonimplanted external receiver.

19. A cardiac monitor for monitoring heart rate variability of a human heart, said monitor being fully implantable beneath the skin of a patient and comprising:
   timing means for timing successive heart monitoring periods;
   electrode means for establishing electrical contact with the heart;
   R wave detecting means coupled to said electrode means for detecting R waves of the heart, during each said heart monitoring period;
   interval determining means responsive to said R wave detecting means for determining the time intervals between adjacent R waves;
   data generating means responsive to said time intervals for generating heart rate data;
   memory means for storing said heart rate data;
   discriminating means for discriminating between normal sinus heart beats and ventricular heart beats;
   factor generating means responsive to the completion of each said heart monitoring period and said stored heart rate data for generating a heart rate variability factor for each said heart monitoring period;
   said memory means for storing said heart rate variability factors; and
   telemetry means for transmitting said heart rate variability factors stored in said memory means to a nonimplanted external receiver.

20. A cardiac monitor as defined in claim 19 wherein said factor generating means includes time domain analysis means for generating a time domain heart rate variability factor and is responsive to only heart rate data associated with adjacent normal sinus heart beats for generating said time domain heart rate variability factor.

21. A cardiac monitor as defined in claim 20 further including sufficient data determining means for determining if a sufficient number of adjacent normal sinus heart beats have occurred during each said monitoring period and wherein said factor generating means generate said time domain heart rate variability factor only if said sufficient number of adjacent normal sinus heart beats have occurred.

22. A cardiac monitor as defined in claim 21 further including clearing means for clearing said stored heart rate data from said memory means after generating said time domain heart rate variability factor or after said sufficient data determining means determines that said sufficient number of adjacent normal sinus heart beats have not occurred.

23. A cardiac monitor as defined in claim 21 wherein said sufficient number of adjacent normal sinus heart beats is equal to or greater than fifty percent of said heart beats being adjacent normal sinus heart beats.

24. A cardiac monitor as defined in claim 19 further including interpolating means responsive to said discriminating means for interpolating heart beat time intervals associated with ventricular heart beats.

25. A cardiac monitor as defined in claim 24 further including second memory means for storing all said time intervals and wherein said telemetry means transmits all said time intervals stored in said second memory means to an external receiver to permit frequency domain processing of all said time intervals.

26. A cardiac monitor as defined in claim 25 wherein said telemetry means is responsive to a command originating from external to the skin of a patient for transmitting all said time intervals stored in said memory means.

* * * * *

UNITED STATES PATENT AND TRADEMARK OFFICE
CERTIFICATE OF CORRECTION

PATENT NO. : 5,411,031
DATED : May 2, 1995
INVENTOR(S) : Barry M. Yomtov

It is certified that error appears in the above-identified patent and that said Letters Patent is hereby corrected as shown below:

| Column | Line | |
|--------|------|---|
| 8 | 4 | after "in", delete "application" |
| 17 | 51 | insert --data-- before "generating means" |
| 17 | 61 | "Generating" should be --generating-- |

Signed and Sealed this

Eleventh Day of July, 1995

Attest:

BRUCE LEHMAN

Attesting Officer       Commissioner of Patents and Trademarks